United States Patent
Cai et al.

(10) Patent No.: US 9,345,853 B2
(45) Date of Patent: May 24, 2016

(54) TUBE ASSEMBLY AND METHOD FOR MAKING THE ASSEMBLY

(75) Inventors: Kevin G. Cai, Cumberland, RI (US); Darnell C. Worley, II, Uxbridge, MA (US)

(73) Assignee: TEKNOR APEX COMPANY, Pawtucket, RI (US)

(*) Notice: Subject to any disclaimer, the term of this patent is extended or adjusted under 35 U.S.C. 154(b) by 542 days.

(21) Appl. No.: 12/928,407

(22) Filed: Dec. 10, 2010

(65) Prior Publication Data
US 2012/0150150 A1   Jun. 14, 2012

(51) Int. Cl.
| | | |
|---|---|---|
| *A61M 25/00* | (2006.01) | |
| *B29C 65/48* | (2006.01) | |
| *B29C 65/00* | (2006.01) | |
| *F16L 33/22* | (2006.01) | |
| *F16L 33/34* | (2006.01) | |
| *B29L 23/00* | (2006.01) | |

(52) U.S. Cl.
CPC ............ *A61M 25/0014* (2013.01); *B29C 65/48* (2013.01); *B29C 65/4895* (2013.01); *B29C 66/1222* (2013.01); *B29C 66/1224* (2013.01); *B29C 66/5344* (2013.01); *B29C 66/636* (2013.01); *B29C 66/73152* (2013.01); *F16L 33/22* (2013.01); *F16L 33/34* (2013.01); *A61M 25/0097* (2013.01); *B29C 66/71* (2013.01); *B29C 66/7392* (2013.01); *B29C 66/7394* (2013.01); *B29C 66/742* (2013.01); *B29C 66/857* (2013.01); *B29K 2995/007* (2013.01); *B29L 2023/007* (2013.01); *Y10T 29/49826* (2015.01)

(58) Field of Classification Search
CPC ...................... A61M 25/0014; A61M 25/0052; A61M 25/0097; A61M 2025/0059; A61M 2025/0098

USPC .......... 604/273, 524–527, 533; 138/137–139, 138/153, 172, 174, 109, 110, 116; 285/45, 285/55
See application file for complete search history.

(56) References Cited

U.S. PATENT DOCUMENTS

| | | | | |
|---|---|---|---|---|
| 4,420,016 | A | * | 12/1983 | Nichols ......................... 138/103 |
| 4,547,194 | A | * | 10/1985 | Moorehead ..................... 604/523 |
| 4,559,046 | A | * | 12/1985 | Groshong et al. ............. 604/524 |

(Continued)

FOREIGN PATENT DOCUMENTS

| | | |
|---|---|---|
| EP | 0 239 244 | 9/1987 |
| EP | 0 356 774 | 3/1990 |

(Continued)

OTHER PUBLICATIONS

"Shore Durometer Conversion Chart". Thermal Tech Equipment Co. Inc. <http://www.ttequip.com/knowledgelibrary/TechPageShoreDurometerConversionChart.htm>. Accessed Jan. 2, 2015.*

(Continued)

*Primary Examiner* — Kami A Bosworth
(74) *Attorney, Agent, or Firm* — Hudak, Shunk & Farine Co. LPA

(57) ABSTRACT

A tube assembly including a flexible tube joined to a connector with the tube having an insert liner located therein at least in an area of a distal end of the connector that provides improved retention force between the tube and connector. Methods for preparing the tube assembly are disclosed and include the use of adhesives or solvent for bonding the tube to the connector.

18 Claims, 1 Drawing Sheet

(56) References Cited

U.S. PATENT DOCUMENTS

| | | | | |
|---|---|---|---|---|
| 4,596,563 | A | * | 6/1986 | Pande .......................... 604/264 |
| 4,723,947 | A | | 2/1988 | Konopka |
| 4,737,152 | A | * | 4/1988 | Alchas ......................... 604/256 |
| 5,224,939 | A | * | 7/1993 | Holman ................ A61M 5/158 604/528 |
| 5,443,781 | A | | 8/1995 | Saab |
| 5,861,200 | A | | 1/1999 | Rowley |
| 5,916,208 | A | * | 6/1999 | Luther et al. .................. 604/508 |
| 6,319,244 | B2 | | 11/2001 | Suresh et al. |
| 7,135,015 | B2 | * | 11/2006 | Dulak ............... A61M 25/0014 604/523 |
| 7,691,321 | B2 | | 4/2010 | Downie |
| 2006/0082156 | A1 | | 4/2006 | Yamada et al. |

FOREIGN PATENT DOCUMENTS

| | | |
|---|---|---|
| EP | 0 368 473 | 5/1990 |
| EP | 0 564 990 | 10/1993 |
| JP | 2006271498 | 10/2006 |
| JP | 2007307302 | 11/2007 |
| WO | WO 2008/086631 | 7/2008 |

OTHER PUBLICATIONS

"Shore (Durometer) hardness test". MicroCoat Technologies. Available <http://www.m-coat.com/Shore%20A-D%20conversion.pdf>. Accessed Jan. 2, 2015.*

* cited by examiner

TUBE ASSEMBLY AND METHOD FOR MAKING THE ASSEMBLY

FIELD OF THE INVENTION

The present invention relates to a tube assembly including a flexible tube joined to a connector with the tube having an insert liner located therein at least in an area of a distal end of the connector that provides improved retention force between the tube and connector. Methods for preparing the tube assembly are disclosed and include the use of adhesives or solvent for bonding the tube to the connector.

BACKGROUND OF THE INVENTION

Flexible tubing is utilized in many different fields for diverse applications. The tubing has been constructed from various materials, including polymeric materials with the choice of material dependent upon factors such as end use, environment; expected product life, and fluid(s) that the tubing will carry or is expected to contact. For example, tubing has been constructed from materials including, but not limited to polyvinyl chloride, polyolefins, polyesters, polyurethanes, acrylonitrile butadiene styrene (ABS), polycarbonates, acrylics, silicone rubbers, thermoplastic vulcanizates, and styrene based thermoplastic elastomers. Polyolefin and styrenic block copolymers can offer chemical and solvent resistance, but may be relatively difficult to adhere to some other polymer substrates using adhesives or solvent bonding.

Many different approaches have been taken to connect tubes or tube-like objects to different substrates.

U.S. Publication 2006/0082156 to Runyan relates to a clamp for use in connecting flexible tubing to a rigid insert fitting. In one described embodiment, the clamp includes a clamp ring having a raised outer portion which is compressible to tighten the clamp about the tubing, and a liner sleeve positioned within the clamp ring, the liner sleeve having first and second sidewall portions, the first sidewall portion having a greater thickness than the second sidewall portion, and the first sidewall portion being positioned under the raised outer portion of the clamp ring.

U.S. Pat. No. 6,319,244 to Suresh et al. relates to a catheter having both a flexible and a rigid reinforcement section. The catheter body is comprised of an elastomeric material, such as silicone, having a resilient coil or spring member within a fluid delivery lumen along the proximal portion thereof. The catheter is provided with a more rigid malleable reinforcement member at the distal portion thereof, also extending within the fluid delivery lumen and positioned proximal the coil member within the fluid delivery lumen. The rigid reinforced distal portion of the catheter body reportedly helps the surgeon to hold the tip of the catheter more firmly, and makes insertion of the catheter tip into the body vessel easier. The more flexible support portion at the proximal portion of the elastomeric catheter body reinforces the catheter to reportedly prevent kinking, yet allows flexibility to facilitate the surgeon to move the proximal portion of the catheter out of the surgical site. The catheter body may be provided with a balloon and a hinge portion, such as defined by an annular detent, to allow the catheter tip to self-align within the body vessel when the balloon is inflated. Both the flexible and rigid reinforcement sections are tubular to facilitate fluid delivery therethrough within through the lumen through which the reinforcement members reside.

U.S. Pat. No. 5,861,200 to Rowley relates to a unitary molded crosslinked polyethylene tubular connector in a metallic sleeve and method for forming the connector with various end configurations. The connector is reportedly a replacement for copper tubes with associated fittings as well as polybutylene tubing.

U.S. Pat. No. 5,443,781 to Saab relates to sterile disposable coverings for endoscopes and similar optical medical instruments are disclosed together with a method for preparing such coverings. By forming a heated polymeric film with a mandrel of appropriate shape and dimensions, relatively long-length, very small diameter, closely-fitting, thin-walled sleeves are produced, each having a thin, substantially inelastic, optically transparent window formed continuously integral with the sleeve at or proximate to the closed, distal end of the sleeve.

U.S. Pat. No. 4,723,947 to Konopka relates to an injection set for use with an external infusion source of fluid such as insulin which injection set is constructed using multiwall tubing. The interior of the multiwall tubing is made of a material which is reportedly insulin compatible, while the exterior of the multiwall tubing is made of a material which reportedly may be solvent bonded. The multiwall tubing facilitates solvent bonding installation of an insert molded needle assembly and a connector to the ends of the tubing without reportedly necessitating the use of and incurring the disadvantages of epoxy bonding.

European Patent Application 0 564 990 A1 to Saiag Industria S.p.A. relates to a connection and/or T-joint including a rigid tubular insert with at least two ends onto which the ends of flexible tubes are force-fitted. A cover of plastics material is molded over the tubular insert and over the ends of the tubes. At least one respective integral, circular sealing lip projects from the internal surface of the end of each tube and engages the external surface of the corresponding end of the insert.

European Patent Application 0 368 473 A2 to Bard Limited relates to a catheter formed of two coaxial tubes and including near the distal end of the outer tube an expandable and contractable retention structure, for example Malecot wings, and at the proximal end of the inner tube a hollow connector for attachment to a fluid supply or drain, comprises actuating means to effect relative sliding movement of the proximal ends of the tubes so as to expand or contract the retention structure, and which means further include a housing secured to the proximal end of the outer tube and so dimensioned that when the retention structure is moved into the contracted position the hollow connector is withdrawn into the housing.

European Patent Application 0 239 244 A1 to Pacesetter Infusion Ltd. relates to an injection set for delivering a fluid to a subcutaneous injection location in a patient which has a soft cannula projecting from a bottom surface of a housing or holding pad. An insertion needle is initially inserted through one or more self-sealing septum layers located in the top of the holding pad, and extends through a fluid chamber contained in the holding pad and through a lumen of soft cannula, with the sharpened tip of the insertion needle extending beyond the end of the soft cannula when the insertion needle is fully inserted. The insertion needle, which allows priming of the injection set, may be removed following installation of the injection set, and fluid may be supplied to the injection set for delivery to the patient. The fluid is supplied to the chamber via an inlet in a direction parallel to the bottom surface of the holding pad.

Japanese Publication No. 2007307302 to Takehiko relates to providing a connector, wherein a continuous internal liquid flow passage can be formed without a gap nor a step concerning the connector, the connection part of a medical instrument, and a medical tube when the medical tube is connected to the connection part of the medical instrument with the use of the connector. The connector includes: an inner cavity where the medical tube and the connection part of the medical instrument to be connected to the medical tube so as to allow a liquid to pass are inserted; and an erected wall for stopping the respective distal ends of the medical tube and the connection part of the medical instrument which are inserted to the inner cavity. The erected wall includes a tapered inner cavity surface, which is enlarged from a tube insertion side to the side of the connection part of the medical instrument. The erected wall of the connector connecting the medical tube to the medical instrument includes a projection part which is arranged on the side surface at the insertion side of the connection part of the medical instrument.

Japanese Publication No. 2006271498 to Asahi Kasei Medical Co Ltd. relates to providing a coupler for a medical instrument which can be rotatably and liquid-tightly connected with a medical tube by attaching and detaching it to and from a liquid port of the medical instrument. The coupler for a medical instrument consists of a coupler part, a connector part and a locking part. The coupler part has: an outer cylinder which can be connected with the liquid port; an inner cylinder housed in the outer cylinder; and a coupling plate for coupling the inner wall intermediate part of the outer cylinder and the outer wall of the inner cylinder air-tightly. The connector part consists of a hollow tube having a projecting stopper outside of its intermediate part and is connected rotatably and liquid-tightly when it is inserted to the inside of the inner cylinder. The locking part is a removal prevention member of the coupler part and the connector part.

WO 2008/086631 to Newsol Technologies Inc. relates to a connectology system comprising a set of mating male connectors and female connectors, the connectors having one or more of the following features: a) two or more independent quarter-turn threads to engage and disengage the connectors; b) a tactile feedback mechanism to indicate completion of engagement and commencement of disengagement; c) flange elements to inhibit touch contamination of the connectors; and d) wing elements to permit application of torque for engagement and disengagement.

When connecting flexible tubing in a female fitting of a connector, especially if the tubing is made of polymer with low surface energy polymers, it is difficult to achieve strong bonding with solvent or adhesive bonding techniques. Therefore, there is need to improve the bonding strength of such flexible tubing to connectors in a tubing and connector assembly.

SUMMARY OF THE INVENTION

In view of the above, it is an object of the invention to provide an assembly including a tube joined to a connector that can be used to transfer fluids, such as a liquid and/or gas, the tube including a reinforcing insert liner located within the tube and providing desirable retention force between the tube and connector.

Another object of the invention is to provide an assembly including a tube having an end joined to a connector having a female fitting that reduces deformation at the points of contact between the tube and connector when a pulling force is applied to the components.

A further object of the invention is to provide an assembly with a flexible tube having a hardness less than the hardness of the connector, and preferably less than a hardness of an insert liner located within the tube.

Still another object is to provide an insert liner within a portion of a flexible tube at least adjacent an end of a female fitting of a connector in which a portion of the tube is connected. The insert liner can have a first end located flush or spaced inwardly from the end of the tube.

Further objects include providing an assembly including a tube having an insert joined to a female fitting of a connector with an adhesive or a solvent via solvent bonding.

Another object is to provide a method for connecting a tube to a female fitting of a connector including the steps of providing the tube with an internal insert liner and inserting the tube into a female fitting of a connector such that the liner is adjacent cross-sectionally, the end of the fitting.

Still a further object is to provide a method for joining a tube in a female fitting of a connector including the steps of inserting an insert liner having a first hardness into a tube having a hardness lower than the first hardness, and providing a coating of one or more of an adhesive and a solvent to an outer diameter portion of an end of the tube, inserting the coated tube end into the female fitting of the connector and allowing the tube to be joined to the connector.

Accordingly, an aspect of the present invention is to provide a tube assembly, comprising a flexible tube having an inner surface or diameter and an outer surface or diameter; a connector having a body with a female fitting having a first orifice; and a second orifice; wherein a fluid can flow through the first orifice and second orifice, the first orifice having an inner diameter, a first end of the tube extending into the first orifice, the tube being joined to the connector; and reinforcing insert liner having a first end and a second end, the liner having a passageway through which fluid can flow between said ends, the liner having an outer surface, wherein the insert liner is located within the tube and having one of the ends either flush with the first end of the tube, spaced from the first end of the tube or extending past the first end of the tube and into the connector, wherein a portion of the outer surface of the liner is in contact with the tube inner diameter thereby reinforcing the tube in the area contacted, and wherein a portion of the liner is located adjacent to the first orifice of the connector.

A further aspect of the present invention is to provide a method for preparing a tube assembly, comprising the steps of inserting a liner having a first end and a second end into an inner diameter of a first end of a tube; and inserting the first end of the tube into a female fitting of a connector and forming a tube assembly, wherein the tube is inserted into the fitting a sufficient distance such that a portion of the liner in the tube is located adjacent a distal end of the female fitting.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

The invention provides a tube assembly having improved retention force between a soft flexible tube and a connector having a female fitting through the use of an insert liner that reinforces the tube in an area of connection to the connector. The reinforcing liner minimizes deformation of the tube at the area of connection and causes a significant increase in the retention force between the tube and connector. The tube assembly design allows tube to connector joining by, for example, one or more of friction, adhesive and solvent bonding.

Figure 1:
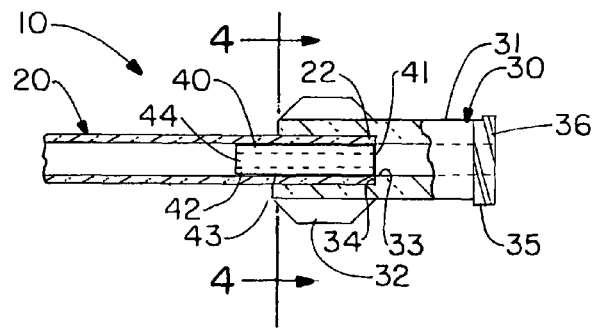
FIG. 1 is a cross-sectional view of one embodiment of a tube assembly according to the present invention having a reinforcing insert liner connected to an inner diameter of a flexible tube, having an end located within a female fitting of a connector, with the liner having an end flush with the end of the tube and also a portion adjacent the distal end of the female fitting of the connector.

Referring now to the drawings, FIG. 1 illustrates one embodiment of a tube assembly 10 of the present invention including a flexible tube 20 having a first end 22 joined to a connector 30. A reinforcing insert liner 40 is located within tube 20.

Tube 20 is formed from a relatively soft composition that allows the tube to be flexible. When utilized herein, the terms "tube" and "tubing" are intended to embrace any construction or structure arranged at a substantially radial distance about a longitudinal axis. The intended use of the tube is as a conduit to convey a fluid such as a gas or liquid, or even a flowable solid, such as in a liquid, or a combination thereof.

The tubing can have one or more of the following features: a hollow cylinder having an inner surface and outer surface, independently, with a circular or non-circular cross-section for example oval, elliptical; a longitudinal axis that is linear or non linear, e.g. bent or curved along all or a portion of the tube length; and one or more of the inner surface and outer surface having a shape that is variable along the length of the tube. The tube can have one or more, two or more, layers with a single layer being preferred.

Depending upon the application, the tubing can be formed having any desired length, inner diameter, outer diameter and wall thickness. The wall thickness is generally defined as the difference between the outer diameter and inner diameter of the tube at a given cross-sectional area.

The composition of the tube can likewise vary based on the requirements of the end use of the assembly. Examples of polymers that can be utilized include, but are not limited to, various polymers, copolymers, thermoplastic elastomers and thermoplastic vulcanizates. Suitable polymers include, but are not limited to, polyolefins, polyvinyl chloride, acrylonitrile-butadiene-styrene resins, silicone homopolymers or block copolymers and polyolefin-styrenic block copolymer based thermoplastic elastomers.

The connector 30 can be any suitable construction that is used as a fitting to join the tube 20 to another component. Many different styles of connectors are known in the art. In the medical field, one common connector is a luer lock-type connector, with one embodiment illustrated in FIG. 1. The connector has a body 31 having at one end a female fitting 32 having an inner surface 33 with an inner diameter that can be constant or variable along the axial length of the inner surface. The flexible tube 20 is joined to the inner surface 33 of connector 30 as explained herein. The female fitting is provided with a seat 34 having an aperture or passageway therein having a diameter less than the diameter of inner surface 33, and preferably a diameter substantially equal to the inner diameter of tube 20 that allows fluid to pass therebetween. The end 22 of the tube 20 preferably contacts the seat 34 upon full insertion into the fitting 32.

At a second end 35, the connector has a second fitting, opposite the first fitting that accepts the tube, a female fitting in the embodiment illustrated. The second fitting may optionally have a taper. The second end 35 preferably includes a threaded external surface 36.

Figure 3:
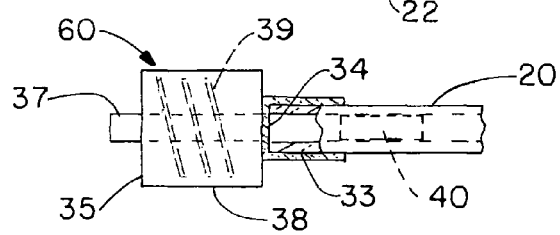
FIG. 3 is a cross-sectional view of a further embodiment of the present invention illustrating a tube assembly wherein a reinforcing insert liner is located within a flexible tube and having an end spaced from the tube end, wherein a portion of the liner is located adjacent an end of a female fitting of the connector of the tube assembly.

FIG. 3 illustrates a connector 60 having a Luer-type male fitting at the second end 35 of the connector 60. The connector illustrated in FIG. 3 also includes the male fitting 37, an inner surface 33 as described hereinabove, as well as seat 34 adapted to abut a flexible tube inserted into the female fitting 32. The male fitting 37 is generally surrounded by an annular locking skirt 38 having a threaded internal surface 39 adapted to interact with the threaded external surface 36 of the connector 30 illustrated in FIG. 1.

The connector is preferably made from a durable polymeric material, but alternatively can be made from metal or other materials. Suitable polymers include, but are not limited to, polyolefins, polycarbonate resins, polyurethane, acrylic resins, polyvinyl chloride, acrylonitrile-butadiene-styrene resins, polyesters, olefin-containing alloys, polyacetyls, cyclic olefin copolymer, polyether ether ketone, polyamide, such as nylon, or a fluorocarbon polymer such as polytetrafluoroethylene.

The flexible tubing joined to the connector is relatively soft and flexible as well as easy to bend and manipulate in actual applications. In preferred embodiments, the tube hardness ranges generally from about 45 Shore A to about 90 Shore A, desirably from about 55 Shore A to about 85 Shore A, and preferably from about 65 Shore A to about 80 Shore as measured according to ASTM D-2240. The connector preferably has a greater hardness than the tube, and desirably from about 70 Shore A to about 100 Shore D, and preferably from about 40 Shore D to about 85 Shore D measured according to ASTM D-2240.

As described herein, there are many different ways to join the tubing to the connector, more specifically the outer surface or diameter of the tubing to the inner surface or diameter of a female fitting of the connector. For example various adhesives can be utilized depending on the composition of the tubing and connector, including, but not limited to, acrylates such as cyanoacrylates, epoxy, silicone, and polyurethane. If desired, primers may be used in association with the adhesive. Suitable adhesive systems are set forth in U.S. patent application Ser. Nos. 12/807,602 and 12/807,604, herein fully incorporated by reference.

Solvent bonding can also be used to join the tubing and connector as known in the art. Solvent bonding or solvent welding generally entails treating one or more surfaces to be joined with a solvent. The solvent is chosen such that it has the ability to soften and swell the surface it is applied to and with the pressure and evaporation of the solvent at the interface between the components to be joined, the two surfaces are bonded. The choice of solvent depends upon the materials utilized. For thermoplastic elastomers based on polyolefin and styrenic block copolymers, cyclohexanone, toluene, xylenes, tetrahydrofuran (THF), 2-methyltetrahydrofuran, and methyl ethyl ketone (MEK), etc. may be used. The end of the tube can be dipped into the solvent for a desired period of time, for example, about 0.5 to about 2 seconds prior inserting the tube end into the connector.

However, even though the tubing and connectors are joined, in some cases differences in materials utilized, e.g. hardness, can lead to deformation of either part, generally the softer material. The deformation can lead to reduction of the retention force between the assembly components. More specifically, in some instances a tube having a lower hardness than the connector can deform when a pulling force is applied between the tube and connector and the tube can be withdrawn from within the connector.

It has been unexpectedly discovered that desirable retention force can be achieved and deformation reduced by providing the tube with an insert liner that reinforces the tube in the area of connection to the connector even if the liner is friction fit inside the tubing and does not adhere to the tubing. However, the insert liner can be adhered to or otherwise connected to the inner surface of the tubing in some embodiments The liner contacts the inner surface of the tube on at least two points, and in some embodiments, preferably more. The insert has a design that permits fluid to pass thereby or therethrough or a combination thereof, see FIG. 9 for example, depending on the cross-sectional shape of the liner.

The Shore A hardness of the insert liner can vary depending on the structure thereof. That said the hardness of the liner is generally greater than or equal to the hardness of the tube. Desirably the insert liner hardness ranges from 85 Shore A to about 100 Shore D and preferably is from 40 Shore D to about 90 Shore D.

The tube insert liner is preferably made from a durable polymeric material, but alternatively can be made from metal or other materials. Suitable polymers include, but are not limited to, polyolefins such as polyethylene and polypropylene, polyolefin copolymers, polycarbonate resins, polyurethane, acrylic resins, polyvinyl chloride, acrylonitrile-butadiene-styrene resins, polyesters, olefin-containing alloys, polyacetals, cyclic olefin copolymer, polyether ether ketone, polyamides, such as nylon, or a fluorocarbon polymer. The insert liner material should be compatible with the composition of the tube as well as the fluid(s) that will come into contact with the liner.

The shape of the insert liner is dependent on factors, a first being the reinforcing contact desired with the tube and a second being the desire to maintain at least a minimum flow past the liner. An additional factor is the desire to keep the liner in place at a set location within the tube, whether having an end of the liner flush with the tube end, located a distance from the tube end or extending past the tube end and into a portion of the connector itself. In a preferred embodiment a snug fit of the insert liner to the inside of the tubing is desired. Additionally, in a preferred embodiment it is desired that in an assembled condition with the tube connected or joined to the connector, the insert liner is located within the tube at a position such that at least a portion of the liner extends outwardly, i.e. in a direction with respect to the longitudinal axis of the tube, or the radial center of the distal end of the connector, from the distal end of the fitting of the connector into which the tube extends, and also preferred that a portion of the liner extends into the fitting, see FIGS. 1 and 2 for example.

Figure 2:
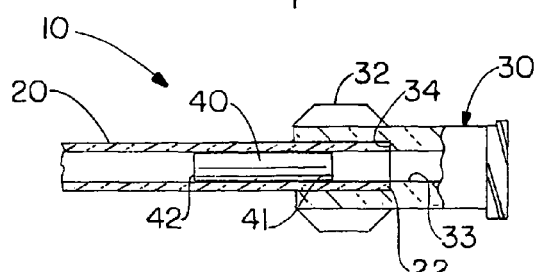
FIG. 2 is a cross-sectional view of a further embodiment of the present invention illustrating a tube assembly wherein a reinforcing insert liner is located within a flexible tube and having an end spaced from the tube end, wherein a portion of the liner is located adjacent an end of a female fitting of the connector of the tube assembly.
Figure 4:
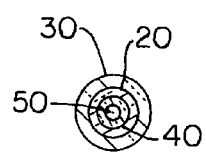
FIG. 4 is a cross-sectional view along line 4-4 of FIG. 1 illustrating the insert liner adjacent the end of the female connector at the point of cross section.

In one embodiment the reinforcing insert liner has an inner surface, preferably a diameter, and an outer surface, preferably a diameter. As illustrated in FIGS. 1-3, the insert liner 40 has a first end 41 and a second end 42 generally disposed along the longitudinal axis of the tube 20. In the embodiment illustrated in FIG. 1, the first end 41 of insert 40 is disposed flush with the end 22 of tube 20. The second end 42 of insert 40 terminates past the distal end 32 of connector 30 and a portion of the insert between the first end and second end is located laterally or radially, with respect to the longitudinal axis of the tube running through the distal end of the fitting, adjacent the distal end of the connector. Insert liner 40 has an outer surface 43 and an inner surface 44. The outer surface in the embodiment illustrated in FIGS. 1 and 4 is cylindrical and contacts the inner diameter of the tube 20 along its length. The inner surface 44 of insert liner 40 in FIG. 1 is also cylindrical and passage of the fluid is thus allowed between the connector 30 and the tube 20.

FIG. 2 shows alternate positioning of insert liner 40 within tube 20. In this embodiment, the first end 41 of the insert liner is disposed a distance from the end 22 of tube 20. The second end 42 of liner 40 extends in the tube past the location where the portion of the tube is adjacent the end 32 of the connector 30.

In FIG. 3 the insert liner 40 is disposed even further within the tube with the first end 41 of insert liner 40 located adjacent the distal end 32 of fitting 30 with a second end 42 of the liner disposed even further away from the end 22 of tube 20.

One consistent feature between the embodiments illustrated in FIG. 1 through FIG. 3 is that a portion of the insert liner 40 is disposed laterally or radially adjacent a distal end of the connector 30 in order to reduce deformation of the tube where it enters connector 30. FIG. 4 illustrates a full cross-section through a line 4-4 of FIG. 1 and shows that the fluid passage 50 located within insert liner 40 which is generally concentric within tube 20 located within fitting 30 at the indicated location.

Figure 5:
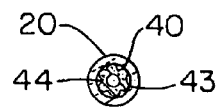
FIG. 5 is a cross-sectional view illustrating a further embodiment of a reinforcing insert liner located within a portion of a tube.
Figure 6:
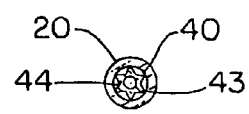
FIG. 6 is a cross-sectional view illustrating a further embodiment of a reinforcing insert liner located within a portion of a tube.

The wall thickness of the insert liner 40 can vary from an outer surface 43 to an inner surface 44 at one or more locations along the length of the insert liner 40, if desired. FIG. 5 illustrates a cross-sectional embodiment of another insert liner 40 that contacts the inner surface of tube 20 intermittently. The outer surface 43 of the liner 40 includes a plurality of rounded ridges and valleys. FIG. 6 presents an alternative embodiment wherein the outer surface 43 of the insert liner 40 includes a plurality of relatively pointed ridges and valleys.

Figure 7:
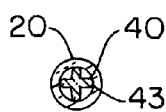
FIG. 7 is a cross-sectional view illustrating a further embodiment of a reinforcing insert liner located within a portion of a tube.

FIG. 7 illustrates a further embodiment of an insert liner 40 of the present invention. The insert liner has a large outer surface area and is generally considered a solid, with no internal passageway extending through an inner portion of the liner. The liner 40 illustrated in FIG. 7 is in the form of an X-shaped construction. The liner thus has an external passageway whereby fluid can flow from the first end to the second end or vice versa. In view of the embodiment illustrated in FIG. 7 it is understood that the insert liners of the present invention can have an outer surface that contacts at least two points of the tube 20, preferably at three or more locations, and most preferably four or more locations, such as shown in FIG. 7.

Figure 8:
FIG. 8 is a cross-sectional view illustrating a further embodiment of a reinforcing insert liner located within a portion of a tube.
Figure 9:
FIG. 9 is a cross-sectional view illustrating a further embodiment of a reinforcing insert liner located within a portion of a tube.

FIGS. 8 and 9 illustrate further embodiments of an insert liner 40 of the present invention having an external passageway by which fluid can flow from a first end to a second end of the insert liner.

EXAMPLES

In order to illustrate the benefits of utilizing the tube assembly of the present invention including an insert liner, the following examples are presented. The tubing utilized had a 4.06 mm (0.16 inch) outer diameter and 2.54 mm (0.10 inch) inner diameter. The tubing was formed from a low-polarity polymer composition, namely thermoplastic elastomer comprising a styrenic block copolymer and a polyolefin. The Shore A hardness of the thermoplastic elastomer is set forth in Table 1. Connectors of the indicated composition were purchased from Qosina of Edgewood, N.Y. The inner diameter of the female fitting of the connector connected to the tube outer diameter was about 4.06 mm (0.16 inch). The rigid thin wall tube liner was translucent amber PEEK Tubing, available from Zeus of Orangeburg, S.C., 2.59 mm (0.102 inch) outer diameter, with 2 mil wall thickness. The liner of 10-14 mm in length was first inserted into one end of the tubing so that the trailing end of the insert was flush with the end of the tube, and then the tubing end was dipped into cyclohexanone or xylene for about 0.5-2.0 seconds. The tubing was pushed into the female connector. If necessary the tubing was adjusted in the connector to allow proper wetting of the connector with the solvent. The retention force of the assembly of the tubing and connector was measured on an Instron tensile instrument at 20 in/min speed with one inch tubing sample length between the Instron clamp and the tubing/connector line. The results of the average retention force of the adhered assemblies are set forth in Table 1 below.

TABLE 1

| Examples | Solvent | Liner | Tubing TPE Material Hardness[1] | Connector | Average Retention Force (lbf) |
| --- | --- | --- | --- | --- | --- |
| Comparative #1 | cyclohexanone | No | 65A | ABS | 4.2 |
| Comparative #2 | cyclohexanone | No | 75A | ABS | 6.1 |
| Comparative #3 | cyclohexanone | No | 85A | ABS | 8.4 |
| 1 | cyclohexanone | Yes | 65A | ABS | 11.6 |
| 2 | cyclohexanone | Yes | 75A | ABS | 12.8 |
| 3 | cyclohexanone | Yes | 85A | ABS | 9.6 |
| Comparative #4 | cyclohexanone | No | 65A | Acrylic | 3.8 |
| Comparative #5 | cyclohexanone | No | 75A | Acrylic | 6.2 |
| Comparative #6 | cyclohexanone | No | 85A | Acrylic | 8.6 |
| 4 | cyclohexanone | Yes | 65A | Acrylic | 8.4 |
| 5 | cyclohexanone | Yes | 75A | Acrylic | 11.1 |
| 6 | cyclohexanone | Yes | 85A | Acrylic | 9.6 |
| Comparative #7 | Xylene | No | 75A | ABS | 6.8 |
| Comparative #8 | Xylene | No | 85A | ABS | 8.9 |
| 7 | Xylene | Yes | 65A | ABS | 9.0 |
| 8 | Xylene | Yes | 75A | ABS | 9.3 |
| Comparative #9 | Xylene | No | 75A | Acrylic | 5.9 |
| Comparative #10 | Xylene | No | 85A | Acrylic | 8.3 |
| 9 | Xylene | Yes | 65A | Acrylic | 10.2 |
| 10 | Xylene | Yes | 75A | Acrylic | 10.7 |

[1]ASTM D-2240

As illustrated in Table 1, the tube assemblies including the insert liner each had a greater retention force when compared to the corresponding tube assembly lacking the insert liner. Thus, the tube assemblies of the present invention including the insert liner located within the tube provide improved retention force between a tube and a connector.

While in accordance with the patent statutes, the best mode and preferred embodiment have been set forth, the scope of the invention is not limited thereto, but rather by the scope of the attached claims.

What is claimed is:

1. A tube assembly, comprising:
a flexible tube having an inner surface or diameter and an outer surface or diameter, wherein the tube is a hollow cylinder;
a connector having a body with a female fitting having a first orifice and a second fitting having a second orifice, wherein the second fitting is either i) a second female fitting having a threaded external surface or ii) a male fitting having an annular locking skirt having a threaded internal surface; wherein a fluid can flow through the first orifice and the second orifice, the first orifice having an inner diameter, a first end of the tube extending into the first orifice and being directly connected to the connector, and the tube outer surface or diameter being directly joined to the connector first orifice inner diameter by one or more of friction, an adhesive, and solvent bonding; and
a reinforcing insert liner having a first end and a second end, the insert liner having a passageway through which fluid can flow between said ends, the insert liner having an outer surface, wherein the insert liner is located completely within the tube and has both ends spaced from each of the first end of the tube and a second end of the tube, wherein a portion of the outer surface of the insert liner is in contact with the tube inner surface or diameter thereby reinforcing the tube in the area contacted, wherein the insert liner is connected to the tube solely by a friction fit and is not adhered to the tube, and wherein a portion of the insert liner is located laterally adjacent to the first orifice of the connector.

2. The tube assembly according to claim 1, wherein cross-sectionally a portion of the tube is located between the first orifice of the connector and a portion of the insert liner.

3. The tube assembly according to claim 2, wherein hardness of the insert liner is 40 Shore D to about 90 Shore D, and wherein hardness of the tube is from about 55 Shore A to about 85 Shore A.

4. The tube assembly according to claim 2, wherein the insert liner outer surface is in contact with the inner surface or diameter of the tube along the length of the insert liner.

5. The tube assembly according to claim 2, wherein the insert liner outer surface is in contact with the inner diameter of the tube intermittently along the length of the insert liner.

6. The tube assembly according to claim 2, wherein the connector female fitting contains a seat that abuts the first end of the tube, the seat having an orifice through which fluid is adapted to flow.

7. The tube assembly according to claim 2, wherein the tube consists of a single layer of material.

8. The tube assembly according to claim 1, wherein the connector is a Luer lock-type connector.

9. The tube assembly according to claim 1, wherein the insert liner has no internal passageway, wherein the liner has an external passage way whereby fluid can flow from a first end to a second end of the insert liner between an outer surface of the insert liner and an inner surface of the tube.

10. A tube assembly, comprising:
- a flexible tube having an inner surface and an outer surface or diameter, wherein the tube is a hollow cylinder;
- a connector having a body with a female fitting having a first orifice and a second fitting having a second orifice, wherein the second fitting is either i) a second female fitting having a threaded external surface or ii) a male fitting having an annular locking skirt having a threaded internal surface; the first orifice having an inner surface, a first end of the tube extending into the first orifice and being directly connected to the connector, and the tube outer surface or diameter being directly joined to the connector first orifice inner diameter solely by friction; and
- a reinforcing insert liner having a first end and a second end, the insert liner having an internal or external passageway, the insert liner having an outer surface, wherein the first end and the second end of the insert liner are both located within the tube and one of the ends is either flush with the end of the tube or spaced from the first end of the tube, wherein a portion of the outer surface of the insert liner is in contact with the tube inner surface thereby reinforcing the tube in the area contacted, wherein the insert liner is connected to the tube solely by a friction fit and is not adhered to the tube, and wherein a portion of the insert liner is located laterally adjacent to the first orifice of the connector.

11. The tube assembly according to claim 10, wherein cross-sectionally a portion of the tube is located between the first orifice of the connector and a portion of the insert liner, and wherein a hardness of the insert liner is 40 Shore D to about 90 Shore D, and wherein hardness of the tube is from about 55 Shore A to about 85 Shore A.

12. The tube assembly according to claim 11, wherein the insert liner outer surface is in contact with the inner surface or diameter of the tube along the length of the insert liner.

13. The tube assembly according to claim 11, wherein the insert liner outer surface is in contact with the inner diameter of the tube intermittently along the length of the liner.

14. The tube assembly according to claim 10, wherein one of the insert liner ends is substantially flush with the first end of the tube.

15. The tube assembly according to claim 10, wherein the insert liner ends are spaced from each of the first end and the second end of the tube, and wherein a portion of the insert liner between the first end of the insert liner and the second end of the insert liner is located laterally adjacent the first orifice of the connector.

16. The tube assembly according to claim 10, wherein the passageway is an external passageway, wherein the liner has an external passageway whereby fluid can flow from a first end to a second end of the insert liner between an outer surface of the insert liner and an inner surface of the tube.

17. The tube assembly according to claim 10, wherein the passageway is an internal passageway.

18. The tube assembly according to claim 10, wherein the connector is a Luer lock-type connector.

* * * * *